United States Patent
Germann et al.

(10) Patent No.: US 11,076,949 B2
(45) Date of Patent: Aug. 3, 2021

(54) INJECTOR WITH TRANSMISSION MECHANISM, IN PARTICULAR GEAR TRAIN

(71) Applicant: MEDICEL AG, Altenrhein (CH)

(72) Inventors: Reto Germann, Frauenfeld (CH); Volker Dockhorn, Altenrhein (CH)

(73) Assignee: MEDICEL AG

( * ) Notice: Subject to any disclaimer, the term of this patent is extended or adjusted under 35 U.S.C. 154(b) by 399 days.

(21) Appl. No.: 15/445,895

(22) Filed: Feb. 28, 2017

(65) Prior Publication Data
US 2017/0245984 A1   Aug. 31, 2017

(30) Foreign Application Priority Data

Feb. 29, 2016 (CH) .......................................... 261/16
Sep. 8, 2016 (CH) ....................................... 1168/16

(51) Int. Cl.
| | |
|---|---|
| *A61F 2/16* | (2006.01) |
| *F16H 31/00* | (2006.01) |
| *F16H 19/04* | (2006.01) |
| *A61M 5/315* | (2006.01) |

(52) U.S. Cl.
CPC ......... *A61F 2/167* (2013.01); *A61M 5/31581* (2013.01); *A61M 5/31586* (2013.01); *A61M 5/31595* (2013.01); *F16H 19/04* (2013.01); *F16H 31/001* (2013.01); *A61F 2/1667* (2013.01); *A61M 2205/581* (2013.01); *F16H 2019/046* (2013.01)

(58) Field of Classification Search
CPC ........... A61M 5/31581; A61M 5/31586; A61F 2/1662; A61F 2/1664; A61F 2/1667; A61F 2/1678; F16H 2019/046

USPC ......................................................... 623/6.12
See application file for complete search history.

(56) References Cited

U.S. PATENT DOCUMENTS

| | | | | |
|---|---|---|---|---|
| 4,820,287 A | * | 4/1989 | Leonard ............ | A61M 5/31581 604/135 |
| 5,772,666 A | * | 6/1998 | Feingold ............... | A61F 2/1664 606/107 |
| 6,342,058 B1 | | 1/2002 | Portney | |

(Continued)

FOREIGN PATENT DOCUMENTS

| | | |
|---|---|---|
| CA | 2618528 A1 | 8/2008 |
| EP | 1491163 A2 | 12/2004 |

(Continued)

*Primary Examiner* — Martin T Ton
(74) *Attorney, Agent, or Firm* — Morriss O'Bryant Compagni Cannon, PLLC

(57) ABSTRACT

An injector for ejecting an intraocular lens into an eye, comprises
  a longitudinal injector body, in which an injector piston rod can be guided in an axially displaceable manner,
  an injector nozzle at a front end of the injector body, in the direction of which the injector piston rod can be displaced,
  a displacement mechanism for pushing the injector piston rod forwards, and
  an actuating element for the manual actuation of the displacement mechanism.
The
  displacement mechanism includes a transmission mechanism, by means of which the actuating element and the injector piston rod can be placed in an articulated driving connection, and
  an operating region for the actuation of the actuating element is formed at a longitudinal side of the injector body.

20 Claims, 8 Drawing Sheets

(56) References Cited

U.S. PATENT DOCUMENTS

| | | |
|---|---|---|
| 7,905,888 B2 | 3/2011 | Brown |
| 8,425,595 B2 * | 4/2013 | Tsai .................. A61F 2/1648 623/6.12 |
| 2005/0149159 A1 * | 7/2005 | Andreas ................ A61F 2/95 623/1.11 |
| 2009/0018548 A1 * | 1/2009 | Charles ................ A61F 2/167 606/107 |
| 2013/0158561 A1 | 6/2013 | Bhagat et al. |
| 2013/0253402 A1 | 9/2013 | Badawi et al. |
| 2014/0222013 A1 * | 8/2014 | Argal .................. A61F 2/1678 606/107 |
| 2015/0342726 A1 * | 12/2015 | Deacon ................ A61F 2/148 623/6.12 |
| 2016/0000556 A1 | 1/2016 | Perera |
| 2016/0120678 A1 * | 5/2016 | Green .................. A61F 2/966 623/1.11 |
| 2020/0015960 A1 * | 1/2020 | Holderby ............. A61F 2/167 |
| 2020/0197167 A1 * | 6/2020 | Wensrich ............. A61F 2/167 |

FOREIGN PATENT DOCUMENTS

| | | |
|---|---|---|
| ES | 1010722 | 2/1990 |
| WO | 2006113138 A1 | 10/2006 |
| WO | 2011155636 A1 | 12/2011 |
| WO | 2014137983 A1 | 9/2014 |

\* cited by examiner

INJECTOR WITH TRANSMISSION MECHANISM, IN PARTICULAR GEAR TRAIN

CROSS REFERENCE TO RELATED APPLICATIONS

This application claims priority to Swiss Patent Application No. 00261/16 filed Feb. 29, 2016 and Swiss Patent Application No. 01168/16 filed Sep. 8, 2016, the entirety of each of which is incorporated by this reference

TECHNICAL FIELD OF THE INVENTION

The field of the present invention includes injectors, in particular for injecting an intraocular lens into an eye.

BACKGROUND OF THE INVENTION

The conventional injectors used in the past for inserting intraocular lenses are either designed in the form of a syringe, which can be operated with one hand but cannot be controlled well, or are designed with a screw thread, which can be controlled more easily. In manual actuation of a screw thread the operator has a less strong force sensation, since in contrast to the implementation in syringe form the thread intercepts and absorbs the force to some extent. However, both hands are required for an injector with a screw thread. An example of a screw thread injector is contained in the published patent application WO2006/113138.

In the disclosure document ES 1010722 an injector is disclosed, which is held like a pin and can be actuated via a slide mechanism on the upper side. However, in this case it is not possible to achieve the good controllability and relatively low force application provided by a screw thread injector.

In the disclosure US 2015/342726 A1 an ocular implant insertion apparatus that includes a plunger driver that is not manually powered is disclosed. For example such an insertion apparatus is designed as a spring driven device. In one embodiment the spring drive is combined with a brake mechanism and including a gear train that connects the brake to a piston for pushing a lens.

Disclosure EP 1491163 A2 presents an ophthalmic lens insertion instrument and package. The lens is ejected into the eye by a movable plunger. For this purpose the plunger is operated by an insertion actuator with a finger wheel. The insertion actuator comprises a pinion rotable by the instrument user to cooperate with rack teeth on the plunger.

In an embodiment in US 2016/000556A1 is disclosed a device for delivering an intraocular lens into an incision on an eye of a patient. Said device has pistol-like exterior design. The manual driving mechanism comprises a rack slidably stored within a tubular member to anteriorly engage with a probe and lens and a pinion having one part functionally coupled to the rack and the other part connected to an actuator handle, so that the pinion translates motion of the actuator handle to move he rack forth and back in the passageway to respectively forward and retract the probe and lens.

WO 2014/137983 discloses a pen style intraocular lens (IOL) injector for delivering an IOL into an eye of a patient which includes an IOL load chamber and connected delivery tube, and a spring-loaded push rod for urging the IOL through the delivery tube and out of a distal tip thereof. The injector includes an actuator that is cocked to compress an automatic delivery coil spring. Cocking the actuator also folds the IOL and may elongate a dual optic IOL. A braking mechanism may be provided to permit control of the spring-biased IOL advancement.

Disclosure U.S. Pat. No. 6,342,058 B1 discloses inter alia a combination forceps and enclavation needle instrument that can be operated by one hand. This instrument may be designed as a mechanical or electrical operating and control system. In any case respective rack and pinion gears and a drive rod enable forward or rearward movement of needle and forceps.

Advantages

An advantage of the present invention is to provide an alternative injector. In particular an advantage is to develop an injector that can be controlled well like a thread, in particular with a low force sensation and at the same time can be operated with one hand. A further advantage is to reduce as far as possible the force to be applied or at least the force sensation for the or during the forward movement of the piston. An excessive tremor of the hand in the case of one-handed operation of an injector should be prevented as a whole. In particular it is an advantage to achieve one-handed operation, with the driving force to push and eject a lens provided by the one-handed operating surgeon's own brawn. In particular the driving force shall be achieved without the support of an inbuilt driving force (such as e.g. an inbuilt driving spring or an inbuilt electrical motor) for pushing and ejecting the lens. The injector is relatively simple and can be manufactured at low cost.

SUMMARY OF THE INVENTION

This invention provides the aforementioned advantages, in that it provides an injector, in particular an injector for ejecting an intraocular lens for the purposes of injecting the latter into an eye, which includes:

a longitudinal injector body in which an injector piston rod is guided in an axially displaceable manner (in particular displaceable along the longitudinal extension of the injector body), an injector nozzle at the front end of the injector body, in the direction of which the injector piston rod is displaceable, a displacement mechanism for driving (or pushing) the injector piston rod forward (i.e. towards the injector nozzle), and an actuating element for the manual actuation of the displacement mechanism.

The displacement mechanism includes a transmission mechanism, such as a manually operating transmission mechanism, by means of which the actuating element and the injector piston rod can be or are placed in a articulated driving connection (in particular so that by means of the actuating element the piston rod can be caused to perform a pushing action).

An operating region for the actuation of the actuating element is provided (formed) at a longitudinal side of the injector body.

The guided injector piston rod in particular is displaceable along the longitudinal extension of the injector body towards the injector nozzle at the front end of the injector body. The displacement mechanism is a transmission mechanism, such as a gear mechanism, through which the actuating element and the injector piston rod are arranged in an articulated driving connection, in particular in a force and/or movement transmitting connection, in particular so that by means of the actuating element the piston rod can be caused to perform a pushing action towards the injector nozzle. The displacement mechanism serves for driving or pushing the injector piston rod forward towards the injector nozzle. By means of the actuating element the displacement mechanism may be actuated manually. At the operating region at a longitudinal side of the injector body the actuating element is accessible for the purpose of manual operation of the piston rod.

The injector according to the invention can be controlled well like a screw thread (i.e. with a low force sensation of a screw thread) and at the same time can be operated with one hand. The displacement movement of the piston rod and thus of the lens can be well controlled when using one hand. According to the invention the force is applied via a toothed gear, i.e. a pinion (optionally via a chain of several inter-engaging toothed gears), which engages on a gear rack and moves the injector forwards. The injector is in this connection is held like a ballpoint pen and the toothed gear is moved with for example the index finger. The operating region is in particular in the front section of the housing, i.e. in the semi-section of the housing that is closest to the nozzle.

In one embodiment the transmission mechanism includes at least one toothed gear, and more preferably the transmission mechanism includes at least one toothed gear and a gear rack, wherein the arrangement of the toothed gear and rack is necessarily such that the toothed gear can act on the gear rack or the gear rack can act on the toothed gear in order to transmit forces and movement.

In another embodiment a transmission mechanism in the sense of present invention comprises e.g. at least two interlinked, force and/or movement transmitting parts (such as e.g. the one toothed gear and the gear rack) and a supporting part (such as e.g. the injector body). In yet another embodiment a screw or screw-like means drivable into an injector body, e.g. a mechanism as presented in WO 2006/113138 A1, notably for pushing an IOL in direction of the longitudinal axis of the screw or screw-like means, does not account for a transmission mechanism.

The transmission mechanism may be a gear mechanism, such as a gear train.

The actuating element can be operated by manually pushing or pulling in the longitudinal direction of the injector body.

Advantageously, the gear train is a rack gearing, in particular including at least one gear rack and at least one first toothed gear, whose teeth act on one another so as to transmit force.

An operating region for the actuation of the actuating element is arranged on the injector body on the gear rack side.

Alternatively, an operating region for the actuation of the actuating element is arranged on the injector body on the rear side of the gear rack.

The teeth of the gear rack and of the first toothed gear act directly on one another, in particular by inter-engagement of the teeth.

Optionally, at least a second toothed gear can be arranged between the first toothed gear and the gear rack in order to transmit force.

Advantageously, the second toothed gear is arranged between the first toothed gear and the gear rack in such a way that its teeth engage on the one hand in the teeth on the first toothed gear and on the other hand in the teeth of the gear rack (in a force-transmitting manner), so that a driving force is transmitted by means of the second toothed gear from the first toothed gear to the gear rack.

In one embodiment, the gear rack is a part, in particular an integral part, of the injector piston rod.

Advantageously, the first toothed gear, can be driven via the actuating element.

The actuating element may be fastened as an operating lever to the first toothed gear.

The actuating element, in particular the operating lever, can be designed as a finger grip.

Advantageously, the operating region has at least one opening in the injector body, by virtue of which the actuating element is accessible for manual actuation, wherein at least a part of the actuating element projects through the opening and from the injector body.

Optionally, the transmission mechanism is implemented so that a manual pulling movement on the actuating element effects a pushing movement of the piston rod, substantially opposed to the pulling movement, in the direction of the injector nozzle.

Alternatively, the transmission mechanism is implemented so that a manual pushing movement on the actuating element effects a pushing movement of the pushing rod, substantially parallel to the manual pushing movement, in the direction of the injector nozzle.

Expediently, the injector body has for the injector nozzle a loading device or a recess for accommodating a loading device, wherein a loading device is arranged or can be arranged in the recess.

Expediently, the loading device has a receptacle space for a lens, a proximal opening for inserting the injector piston rod and distal openings for ejecting the lens.

Optionally, the injector body has in addition to a distal opening, which leads to the injector nozzle, a proximal opening, wherein the injector piston rod can by pushing be introduced into the proximal opening in the injector body and the injector piston rod can by actuation of the actuating element be moved forwards in the direction of the injector nozzle.

Expediently, the injector nozzle is provided with a proximal opening and a distal opening, wherein the injector piston and its tip can by being pushed forwards extend through the proximal opening in the direction of the distal opening.

Advantageously, the injector nozzle is arranged at a distance from the injector body on a holder, which connects the injector nozzle to the injector body, wherein the distance between the injector nozzle and the injector body is dimensioned so that the loading device can be arranged in the recess.

The lens may be an intraocular lens.

Expediently, the first toothed gear and optionally the second toothed gear, if present, is implemented as a spur gear.

Advantageously, the injector is designed for one-handed operation.

The actuating element may be designed so that a movement for the actuation of the actuating element occurs substantially along the length of the piston rod, in particular in the direction of the piston rod movement or alternatively in the opposite direction to the piston rod movement.

Optionally the injector comprises a ratchet mechanism for inhibiting a backwards movement of the injector piston rod. The ratchet mechanism comprises a linear rack structure on the injector piston rod and a pawl attached to the injector body. Pawl and linear rack may be engaged preventing motion of the piston rod in a backward direction but allowing motion of the piston rod in a forward direction. For this purpose it is advantageous that the teeth of the linear rack of the ratchet mechanism are asymmetrical, each tooth having a moderate slope on one edge for unhindered movement of the linear rack in one direction (forward direction) and a much steeper slope on the other edge for restriction of movement of the linear rack by the pawl in the other direction (backward direction). The pawl e.g. is a pivoting, optionally spring-loaded finger. Optionally the injector comprises a ratchet mechanism activating element, e.g. in the form of a switch for setting the pawl in an position where pawl and rack are engaged and thus the ratchet mechanism active. The ratchet mechanism comprises at least two settings an inactivated pawl position and an activated pawl position. The pawl engages the teeth of the linear rack, when the ratchet mechanism is activated. If the ratchet mechanism is inactivated, then a forward and backward movement of the piston rod is possible depending on the operators finger movement on the actuating element (finger wheel). If the ratchet mechanism is activated, then substantially a forward movement of the piston rod is possible only (a backward movement by and large is prevented by the ratchet mechanism). When the backward movement of the piston rod is prevented, also—due to a force and motion transmitting connection between the actuating element and the piston rod via the transmission mechanism—the actuating element is prevented from being reset.

Advantageously, the piston rod is provided at its tip with a deformable plunger, in particular an elastic or viscoelastic plunger, such as e.g. a silicone plunger.

The nozzle comprises a distal end having a cross section smaller than 3.1416 mm$^2$ (square millimeter), or less than 3.0 mm$^2$, or less than 2.8 mm$^2$.

The aforementioned optional features can be accomplished in any desired combination so long as they are not mutually exclusive.

Additional advantages of the present invention follow from the following description.

The injector includes a longitudinal body, in particular formed as a housing, with a loading chamber for a lens and a nozzle through which the lens can be ejected. In addition, the injector contains a piston rod that is displaceably supported on or in the body, as well as a transmission mechanism, such as in particular a gear train or rack gearing, by means of which the piston rod can be actuated for the purposes of ejecting a lens, in particular in that the piston rod can be driven forwardly through the loading chamber into the nozzle.

To eject a lens from the injector according to the invention the lens, which is initially located in the loading chamber of the injector, is driven by means of the piston rod from the loading chamber through the injector nozzle into the eye. According to the invention, the drive of the piston rod is effected via the transmission mechanism, in particular the gear train or rack gearing, by means of which the piston rod can be driven forwardly. The transmission mechanism is preferably operating manually, thus preferably the transmission mechanism is driven by manual force and therefore the displacement of the piston rod and in particular the forward movement of the piston rod is effected manually, i.e. by brawn of the human operator only. For this purpose, the injector can be held by one hand and operated at the same time by the same hand. A driving force (such as e.g. a spring drive) other than human brawn is not required for driving the plunger rod and therefore moving and inserting a lens towards and into an eye.

The ejection of the lens on driving the forward movement of the piston rod by the transmission mechanism, in particular the gear train or rack gearing, proceeds in a controlled manner, while the treating physician simply needs one hand to hold the injector and eject the lens. The second hand is free to carry out other manipulations on the patient.

BRIEF DESCRIPTION OF THE FIGURES

Further advantages and features of the invention follow from the following detailed description of an exemplary embodiment of the invention and with reference to the schematic representations, which are not true to scale, in which.

DETAILED DESCRIPTION OF THE INVENTION

Figure 1:
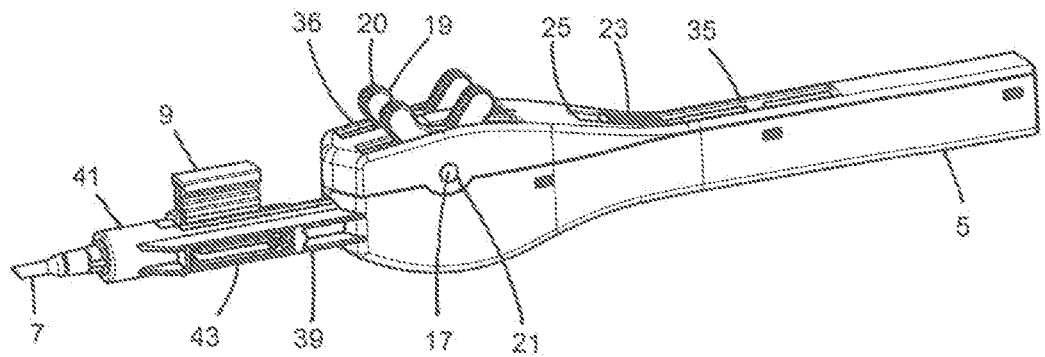
FIG. 1 is an oblique view of an injector according to the invention.

In the following the same reference numerals apply to the same elements in different figures.

Figure 2:
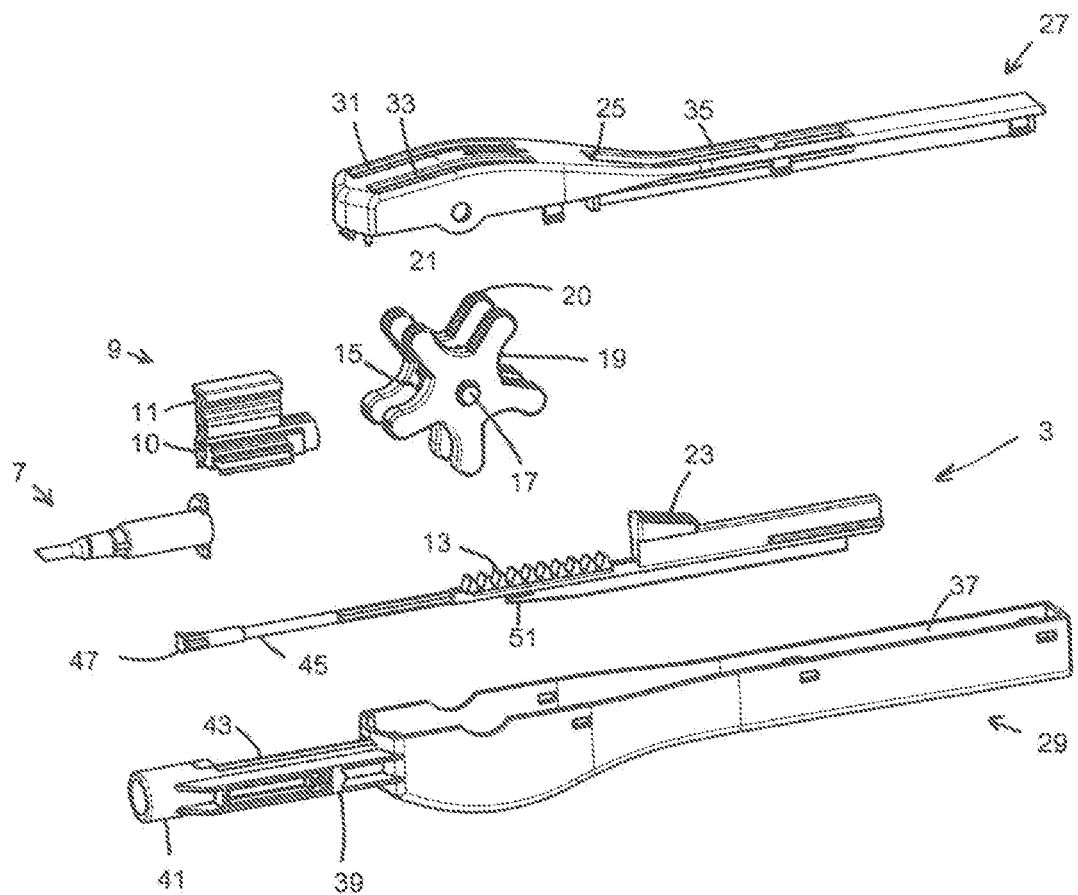
FIG. 2 is an exploded view of an injector according to the invention.
Figure 3:
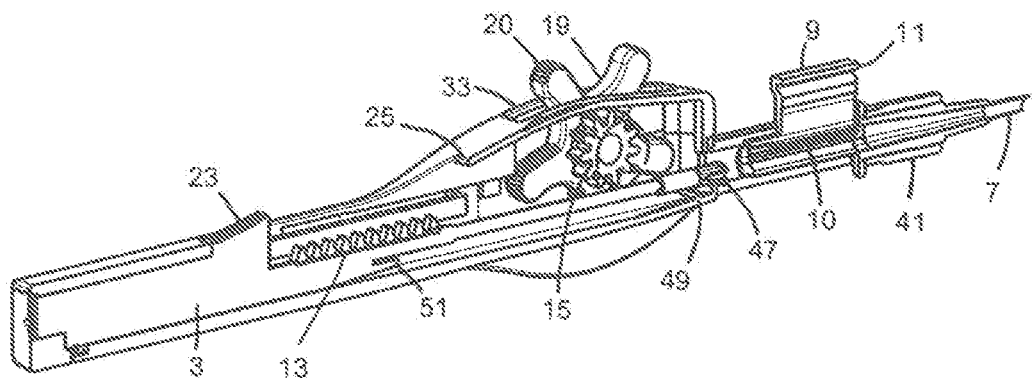
FIG. 3 is a sectional view of an injector according to the invention, and piston rod in a first position (normal position)
Figure 4:
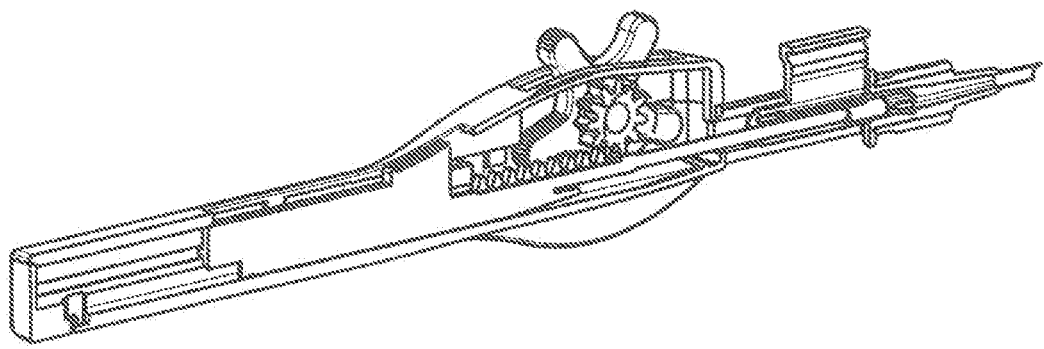
FIG. 4 is a sectional view of an injector according to the invention, and piston rod in a second position (start position)
Figure 5:
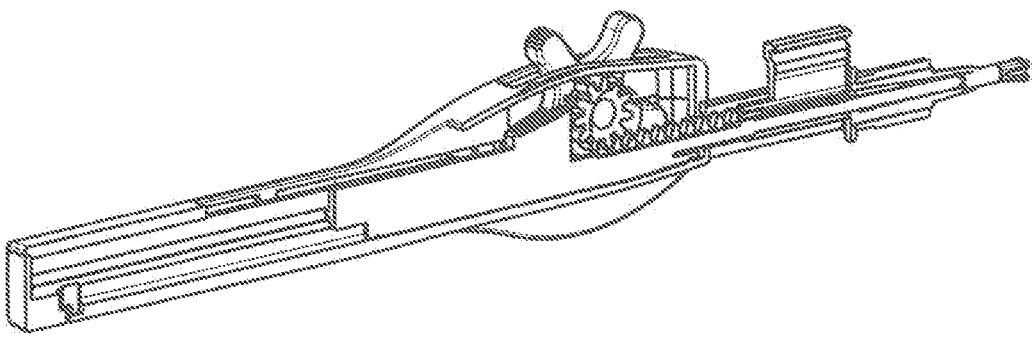
FIG. 5 is a sectional view of an injector according to the invention, and piston rod in a third position (end position)

In a first exemplary embodiment FIG. 1 shows schematically in an oblique view an injector 1 with a gear train, in particular a rack gearing, for an intraocular lens. In FIG. 2 the injector is illustrated in an exploded view. FIGS. 3, 4 and 5 show in each case a sectional view of the injector 1 with different positions of the piston rod 3.

The injector 1 includes a longitudinal housing 5 with a nozzle 7 located at the end of the housing, the nozzle 7 forming the front part of the injector. A displaceable piston rod 3 is supported in the housing 5, the piston rod 3 can be driven forwardly in the direction of the nozzle 7 in order to eject a lens through the nozzle 7 (FIG. 3). A loading device 9 with a loading chamber 10 for a lens (not shown) is provided behind the nozzle 7. The lens can be ejected from the loading chamber 9 and through the nozzle 7 by driving or pushing the piston forwards. The loading device 9 is designed as a cartridge, which can be used with the lens inserted therein. The cartridge comprising a lens may be inserted into the injector. The loading device 9 or in particular the cartridge 10 can be formed for example from two half shells, each of a clamping closure 11.

A gear rack (i.e. a linear gear) 13, which cooperates with a toothed gear (i.e. a pinion, such as a circular gear) 15, is formed on the piston 3. The gear rack 13 and toothed gear 15 form a transmission mechanism, in particular a rack gearing. By manually actuating the toothed gear 15 the piston 3 can be moved backwards and forwards since the teeth of the gear train 13 and tooth gear 15 engage with one another. In the rack gearing the gear rack is a linear machine element with a row of elevations, i.e. the teeth, in which a tooth gear (i.e. pinion) engages. The toothed gear 15 is manually driven by means of at least one actuating element 19, which is firmly connected to the toothed gear 15. The actuating element 19 is formed as a lever, suitably as a lever wheel enlarged compared to the diameter of the toothed gear 15, and in particular as an impeller with radially projecting gripping parts 20. The actuating element 19 is further also depicted as butterfly wheel.

The toothed gear 15 comprises a rotation shaft 17. The actuating element 19 advantageously has the same rotation shaft 17. The rotation shaft 17 of the toothed gear 15 is supported in the housing. An indentation 21 for example is provided in the housing 5 for supporting the rotation shaft 17 of the toothed gear 15. The actuating element 19 and in particular the individual gripping parts 20 of the actuating element 19 project at least partially from the housing 5, while the toothed gear 15 is positioned within the housing circumference and within the housing 5. The housing 5 is optionally formed as an arch around the toothed gear 15 so as to completely accommodate the transmission mechanism in the housing 5. The housing has however openings 31, 33 for the actuating element 19 and in particular its gripping parts 20, so that the actuating element 19 can be manually operated.

The toothed gear 15 is on account of its function arranged on the teeth row side of the gear rack 13 (i.e. on the gear rack side), optionally at an extension of the gear rack displacement path, over the row of teeth of the gear rack 13, so that the teeth of the toothed wheel 15 engage or can engage in the teeth of the gear rack 13. Access to the actuating element 19 is enabled on account of the structure of the housing on the gear rack side. Accordingly, in this first embodiment with only one toothed gear 15 the actuating movement for driving the piston rod 3 forwards is a tractive movement. The finger tractive movement and the resulting forward drive movement of the piston rod 3 are opposed to one another.

The piston rod 3 advantageously comprises a sliding element 23, via which the piston rod 3 can be displaced manually from the normal position to a start position, from which the piston rod 3 can be displaced further in a controlled manner in the direction of the nozzle 7 by means of the actuating element 19. The sliding element 23 is installed for example as illustrated in the embodiment in FIG. 2 on a longitudinal side of the piston rod, such as on the side behind the gear rack 13. In the start position the teeth of the toothed gear 15 and gear rack 13 engage one another for the first time, i.e. the toothed gear 15 engages the first (i.e. front) tooth of the gear rack 13 or can engage the first (i.e. front) tooth of the gear rack 13 on engaging the actuating element.

FIG. 4 shows the aforementioned start position. In this position the piston rod 3 is pushed forward until at least the first tooth (i.e. the front tooth) of the gear rack 13 is engaged by the toothed gear 15 or can be engaged by turning the actuating element 19.

The housing 15 is shaped so that the sliding element 23 in the normal position of the piston rod 3 projects from the housing 5. The housing 5 has in particular a slit-like opening 35, which is aligned parallel to the longitudinal direction of the housing and through which the sliding element 23 projects for the purposes of manual actuation. Where the start position is reached the housing forms a camber with a gap 25 relative to the sliding element 25, underneath which the sliding element 23 can slide into the housing 5 when the piston 3 is advanced by means of the actuating element 19 from the start position further in the direction of the nozzle 7.

The housing 5 is advantageously composed of for example at least one first housing part and a second housing part, such as an upper housing part 27 and a lower housing part 29, which can be assembled, in particular interlocked. The rotation shaft 17 of the toothed gear 15 is supported in an indentation 21 in the upper housing part 27. Furthermore, the upper housing part 27 has the openings 31, 33, 35 for the actuating element 19 and in particular the gripping parts 20 of the actuating element 19 and the sliding element 23 on the piston rod 3. The lower housing part 29 advantageously comprises a receptacle 37 for the piston rod 3, in which the piston rod 3 can be inserted, before the upper housing part 27 with the toothed gear 15 is mounted on top. The point of access to the actuating element 19 is provided on the upper housing part and is identified by the operating region 36.

In the present embodiment a support 39 with a nozzle holder 41 and cartridge receptacle 43 is formed on the lower housing part 29. Alternatively, an arrangement of nozzle holder and/or cartridge receptacle on the upper housing part is conceivable. The cartridge receptacle 43 could if desired also be formed as an integrated loading device with loading chamber.

The piston rod 3 can be provided at its tip 45 with a tappet 47, also referred to as plunger. The tappet or plunger may be deformable, in particular elastic or viscoelastic. The piston rod 3 may be provided with a silicone plunger tip. The nozzle-side tip 45 of the piston rod serves for pushing the lens.

The mode of operation of the injector 1 can be seen in FIGS. 3, 4 and 5.

The injector is used in particular for injecting an intraocular lens into an eye. In this connection a lens, which is initially located in the loading chamber 10 of the injector, can be ejected by means of a piston rod 3 from the loading chamber 10 through the injector nozzle 7 into the eye. According to the invention the drive of the piston rod 3 is effected via a toothed wheel 15, which engages on a gear rack 13 and moves the piston rod 3 forwards. The injector 1 is in this case held with one hand (e.g. like a ballpoint pen) and the toothed wheel 15 and in particular its actuating element 19 is moved with a finger of the same hand (for example with the index finger). In the embodiment according to FIGS. 1-5 the actuating element 19, which is for example formed as an impeller, can be turned with the finger in several pulling movements so that the gear rack 13 and thus the piston rod 3 moves forward (in particular opposite to the pulling movement of the finger) to the nozzle 7 and thus displaces the lens in the direction of the nozzle 7 and from the latter (FIG. 5).

So that the piston rod 3 itself is not inserted into the eye, conveniently a stop means 49 for the piston rod 3 is provided in the housing 5. The piston rod 3 comprises in particular a catching device 51, which blocks the forward movement on the stop means 49. The catching device 51 may be formed as a spring member projecting from the piston rod and inclined relative to the housing, which during the forward movement engages on the stop means 49, which is optionally formed as or with a housing constriction, and on account of its spring action gently dampens and ultimately stops the forward movement of the piston rod 3. The stopped end position of the piston rod is illustrated in FIG. 5.

Before the injection into the eye (as described above) can be carried out, the injector 1 normally has to be made ready beforehand. In particular, the piston rod 3 and lens have to be brought into position. This may take place in the following way.

The lens is placed in the loading chamber 10 and the cartridge with the preloaded lens inserted into the loading chamber 10 is inserted into the injector. With hydrophobic lenses, i.e. lenses that are stored dry, the lens can also already be inserted in the factory by the lens manufacturer. The piston rod 3 is pushed forwards from the normal position (FIG. 3) by means of a sliding element 23 up to the start position, i.e. until the teeth of the toothed gear 15 and gear rack 13 inter-engage (FIG. 4). In the start position, the teeth of the toothed gear 15 and gear rack 13 engage with one another for the first time. When the piston rod 3 is displaced forwardly from the normal position (FIG. 3) to the start position (FIG. 4) the lens in the loading chamber 10 is caught by the piston tip 45 and in particular the tappet 47 mounted thereon and a first part is pushed forwards from the loading chamber 10 into a first partial section of the nozzle 7. In order to displace the piston rod 3 forwards from the normal position (FIG. 3) to the start position (FIG. 4) the piston rod 3 is first of all moved forwards manually by means of the sliding element 23 from the normal position (FIG. 3) until the sliding element is for example flush with the housing 5 (FIG. 4) or alternatively reaches a marker on the housing. If necessary, the pressure on the lens can be temporarily released by holding or withdrawing the piston rod 3 by means of the sliding element 23. The forward displacement of the piston rod 3 from the normal position (FIG. 3) to the start position (FIG. 4) can be executed for example by an assistant or by the doctor, i.e. surgeon, himself. The assistant hands the injector 1 with the piston rod 3 in the start position to the doctor. The doctor uses the butterfly wheel 19 in order to eject the lens by further forward displacement of the piston rod 3 (possibly up to the end position (FIG. 5)) and inject it into an eye. On using the butterfly wheel 19 the sliding element 23 is retracted into the interior of the housing in the further course of the forward displacement of the piston rod.

The ejection of the lens on driving the forward movement of the piston 3 by the gear train is constantly monitored, while the doctor simply needs one hand to hold the injector and to eject the lens. The second hand is free for other manipulations on the patient. Fine pulling movements of a finger on the butterfly wheel are sufficient to insert the lens into an eye. The pulling movement of the finger is regarded as particularly ergonomic since the hand is designed anatomically as a gripping hand and gripping movements of the fingers are therefore less sensitive to pressure than pushing movement.

However, multistage transmission mechanisms may be formed by adding further toothed gears (for example intermediate toothed gears). If for example a second toothed gear were inserted between the first toothed gear 15 and the gear rack 15, the actuating element 19, in particular the butterfly wheel, would now only have to be moved forwards in order to drive the piston rod 3 forwards (i.e. to the nozzle 7). The drive movement could be accomplished with a finger by turning the butterfly wheel 19 forwards. The manual displacement movement would thus correlate to the piston movement. A corresponding gear train in an alternative injector is illustrated in FIGS. 6-10.

Figure 6:
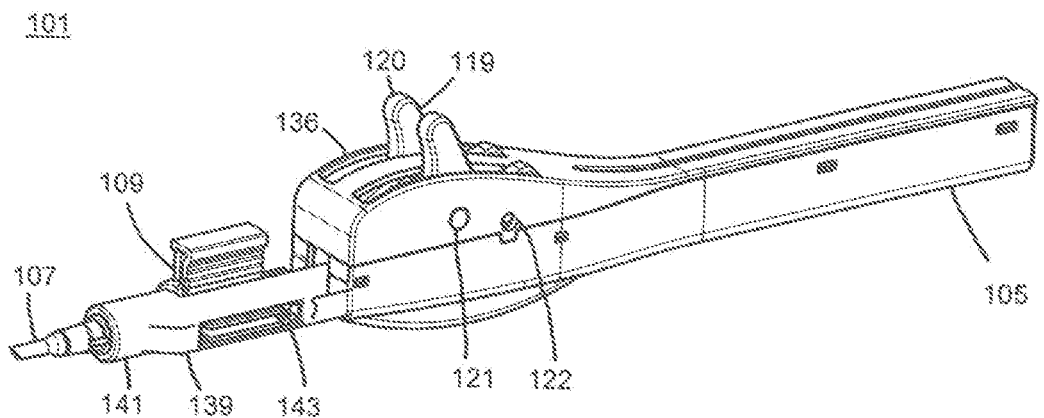
FIG. 6 is an oblique view of a further injector according to the invention.
Figure 7:
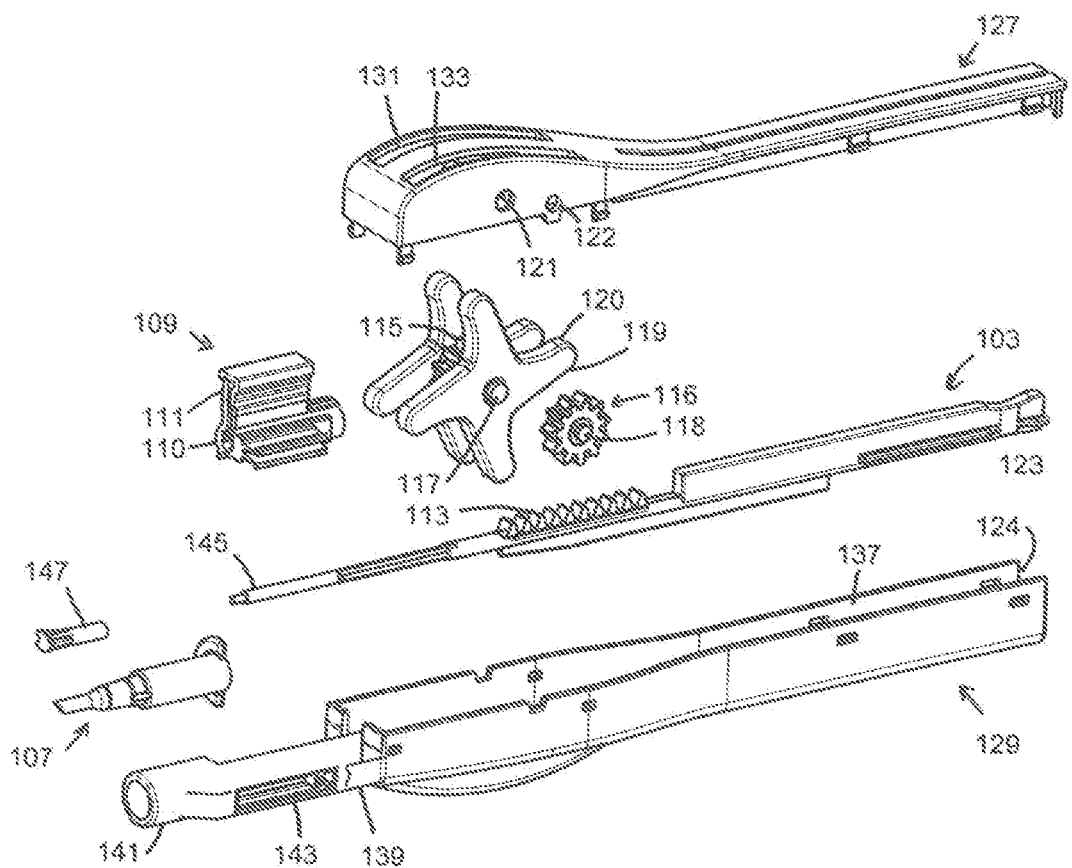
FIG. 7 is an exploded view of the further injector according to the invention.
Figure 8:
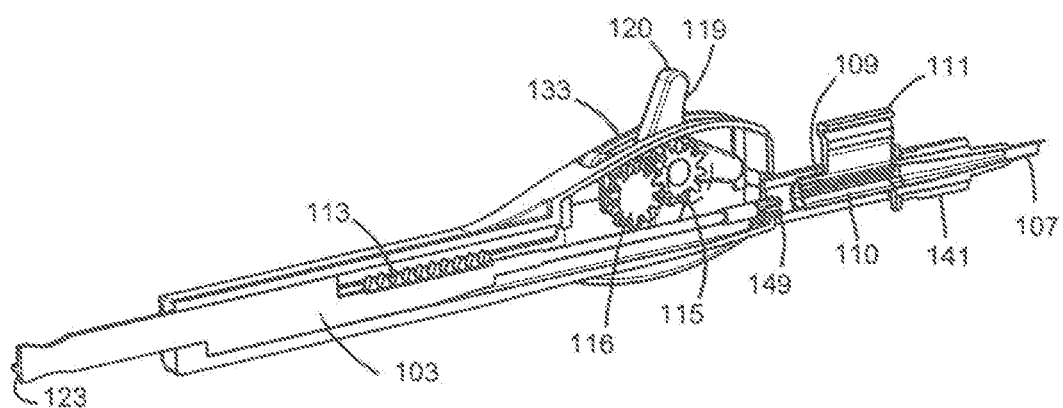
FIG. 8 is s sectional view of the further injector according to the invention, and piston rod in a first position (normal position)
Figure 9:
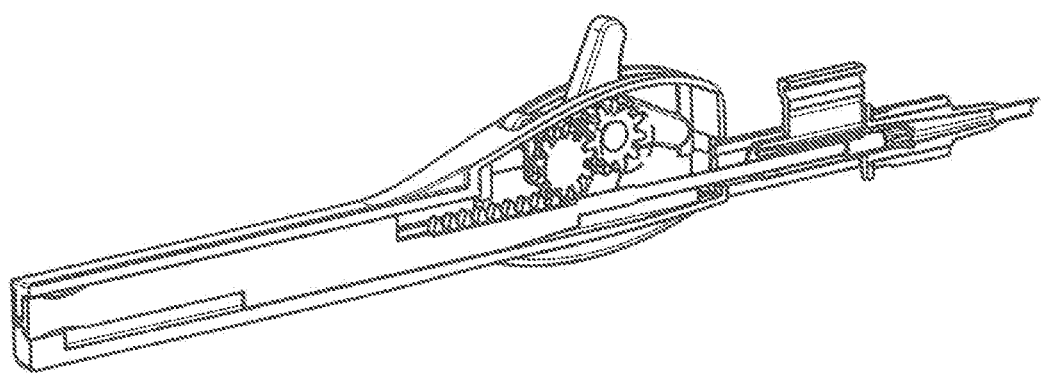
FIG. 9 is a sectional view of the further injector according to the invention, and piston rod in a second position (start position)
Figure 10:
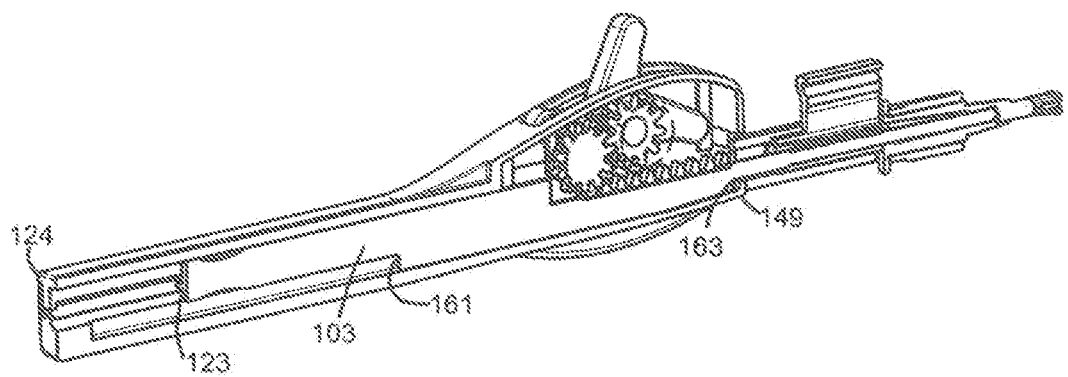
FIG. 10 is a sectional view of the further injector according to the invention, and piston rod in a third position (end position)

In a second exemplary embodiment FIG. 6 shows schematically in an oblique view an injector 101 with a gear train, in particular a rack gearing with two toothed gears and a gear rack, for an intraocular lens. The injector 1 is shown in an exploded view in FIG. 7. FIGS. 8, 9 and 10 show in each case a sectional view of the injector 101 with different positions of the piston rod 103. Differences of this second exemplary embodiment according to FIGS. 6-10 compared to the previously described first exemplary embodiment according to FIGS. 1-5 will be discussed hereinafter.

The injector 101 includes a longitudinal housing 105 with a nozzle 107 located at the end of the housing, wherein a displaceable piston rod 103 is supported in the housing 105 and wherein said piston rod 103 can be pushed forwards in the direction of the nozzle 107 so as to eject a lens through the nozzle 107 (FIGS. 8-10).

A gear rack 113 is formed on the piston 103, which cooperates with a first toothed gear 115 by means of an intermediately located second toothed gear 116. The gear rack 113, first toothed gear 115 and second toothed gear 116 form a transmission mechanism, in particular a rack gearing. By manually actuating the first toothed gear 115 the piston 103 can be moved backwards and forwards, in so far as on the one hand the teeth of the gear rack 113 and second toothed gear 116 and on the other hand the teeth of the second toothed gear 116 and first toothed gear 115 inter-engage. The first toothed gear 115 is manually driven by means of at least one actuating element 119, which is rigidly connected to the first toothed gear 115. The actuating element 119 is formed as a lever, advantageously as a lever wheel enlarged compared to the diameter of the first toothed gear 115, and in particular is formed as a butterfly wheel with radially projecting gripping parts 120.

The first toothed gear 115 has a first rotation shaft 117. The actuating element 119 advantageously has the same rotation shaft 117. The second toothed gear 116 has a second rotation shaft 118. The rotation shafts 117 and 118 of the two toothed gears 115 and 116 are supported in the housing. In order to support the rotation shafts 117 and 118 each is provided with an indentation 121 and 122 in the housing 105. The toothed gears 115 and 116 are positioned within the circumference of the housing or within the housing 105, i.e. completely in the interior of the housing 105.

The housing has a proximal opening 124. The piston rod 103 projects in its normal position beyond the proximal opening 124 from the housing 105 (FIG. 8). The piston rod 103 has a step 161, which prevents the piston rod from entirely sliding out of the housing through the proximal opening 124. By manually pushing on the piston rod 103 at its proximal end 123 the piston rod 103 can be manually displaced (similar to pushing the sliding element 23 in the first exemplary embodiment FIG. 3) from the normal position (FIG. 8) to a start position (FIG. 9). From the start position (FIG. 9) the piston rod 103 can in a second step be displaced further in a controlled manner by means of the actuating element 119 in the direction of the nozzle 107. In the start position (FIG. 9) the teeth of the second toothed gear 116 and of the gear rack 113 engage one another for the first time, i.e. the toothed gear 116 engages the first (i.e. front) tooth of the gear rack 113 or can after a certain rotation of the actuating element 119 engage this first tooth of the gear rack 113.

The housing 105 is advantageously composed of for example at least one first housing part and a second housing part, such as an upper housing part 127 and a lower housing part 129, which can be assembled or interlocked. The first rotation shaft 117 and the second rotation shaft 118 are supported in each case in a pair of indentations 121, 122 in the upper housing part 127. In addition the upper housing part 127 has openings 131, 133 for the actuating element 119, in particular the gripping parts 120 of the actuating element 119, and possibly also an opening for the proximal end of the piston rod 123. The lower housing part 129 advantageously has a receptacle 137 for the piston rod 103, into which the piston rod 103 can be inserted, such as before the upper housing part 127 with the toothed gears 115, 116 is mounted on top. Access to the actuating element 119 is allowed on the gear rack side. The point of access to the actuating element 119 can be denoted as the operating region 136.

The mode of operation of the injector 101 can be seen from FIGS. 8, 9 and 10.

Like the injector 1 shown in FIGS. 1-5, the injector 101 serves in particular for injecting an intraocular lens into an eye. In this way a lens, which is initially located in the loading chamber 109 of the injector, is ejected by means of a piston rod 103 from the loading chamber 109 through the injector nozzle 107 into the eye. According to the invention the drive of the piston rod 103 is effected via a first toothed gear 115 and a second toothed gear 116, wherein the first toothed gear 115 engages in the second toothed gear 116 in order to drive the latter, and the second toothed gear 116 in turn engages a gear rack 113 in order to move the piston rod 103. The injector 101 is held in one hand (e.g. like a ballpoint pen) and at the same time the first toothed gear 115 and in particular its actuating element 119 is moved with a finger of the same hand (for example with the index finger). Since the first toothed gear 115 acts on the second toothed gear 116 and this in turn acts on the gear rack 113 of the piston rod 103, the piston rod 103 can be moved by actuation of the actuating element 119. In the embodiment according to FIGS. 5-10 the actuating element 119, which is advantageously formed as a butterfly wheel, can be turned with the finger in several pushing movements so that the gear rack 113 and thus the piston rod 103 (correlated with the pushing movement of the finger) is moved towards the nozzle 107 and thereby displaces the lens in the direction of the nozzle 107 and ejects it from the latter (FIG. 10).

So that the piston rod 103 itself is not inserted into the eye, advantageously the gear rack 113 is formed at most just long enough so that the tip of the piston rod 103 can be pushed forwards at most approximately to the nozzle opening. A step 163 in the piston rod 103, which abuts against the housing or a stop means 149, can prevent the piston rod 3 from sliding further forwards. The slide element 23 of the first exemplary embodiment (FIGS. 1-5) also acts in the same way, in that it acts on the toothed gear 115, or can be appropriately implemented so that it acts in this or a similar way.

Before the injection into the eye (as described above) can be carried out, the injector 101 normally has to be made ready. In particular, the piston rod 103 and lens have to be brought into position. This may take place as follows. The lens is placed in the loading chamber 110 and in particular the cartridge together with the lens preloaded into the loading chamber 110 is inserted into the injector. In the case of hydrophobic lenses, i.e. lenses that are stored dry, the lens can also already be inserted in situ at the factory by the lens manufacturer. The piston rod 103 projecting in the normal position (FIG. 8) from the housing is pushed forward from the normal position (FIG. 8) by means of manual pressure on the rear side of the piston 123 to the start position, i.e. until the teeth of the toothed gear 116 and gear rack 113 engage (FIG. 9). In the desired start position (FIG. 9) the end of the piston rod lies flush against the housing 105. Before the whole piston rod 103 is inserted into the housing 105, if necessary the pressure on the lens can temporarily be relieved by maintaining or withdrawing the piston rod 103. The forward displacement of the piston rod 103 from the normal position (FIG. 8) to the start position (FIG. 9) can for example be carried out by an assistant or by the doctor himself. If the preparation is carried out by an assistant, the injector 101 advantageously with the piston rod 113 in the described start position is handed to the doctor carrying out the treatment. The doctor operates the butterfly wheel 119 in order to eject the lens by further forward displacement of the piston rod 103 (optionally to the end position (FIG. 10)) and inject it into an eye.

Similarly to the first exemplary embodiment (FIGS. 1-5), according to the second exemplary embodiment (FIGS. 6-10) the ejection of the lens by driving the forward movement of piston rod 103 via the gear rack train proceeds in a controlled manner, while the doctor simply needs one hand to hold the injector and to eject the lens. The second hand is free for other manipulations on the patient. Fine pushing movements of a finger on the butterfly wheel are sufficient to insert the lens into an eye.

In both the afore-described exemplary embodiments (FIGS. 1-5 or FIGS. 6-10) the injector 1, 101 is formed as a bulge on the upper side, in the region of the actuating element 19 or 119 projecting from the housing 5, 105. If—as is shown hereinafter in a third exemplary embodiment (FIGS. 11-15)—the position of the toothed gear or gears is located underneath the gear rack, the upper side of the housing can be formed flatter or flat (for example as a flat surface).

Figure 11:
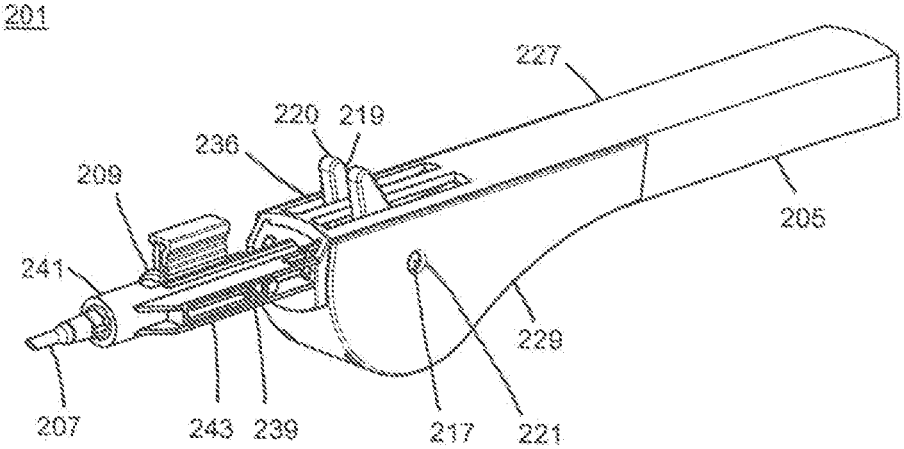
FIG. 11 is a oblique view of a further injector according to the invention.
Figure 12:
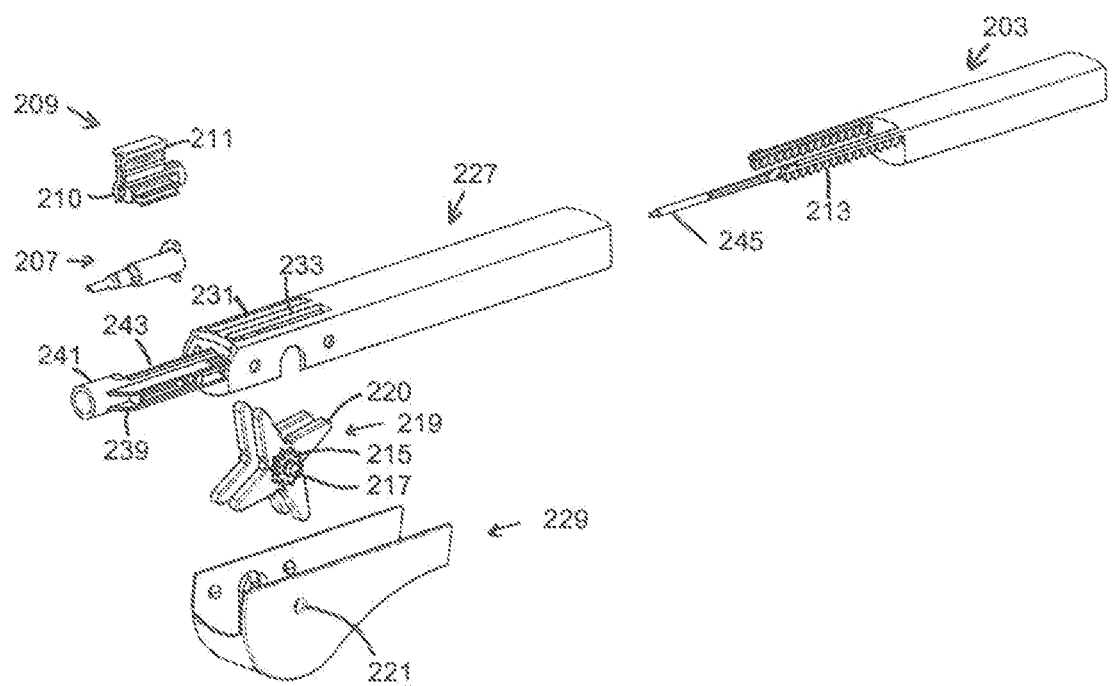
FIG. 12 is an exploded view of the further injector according to the invention from FIG. 11.
Figure 13:
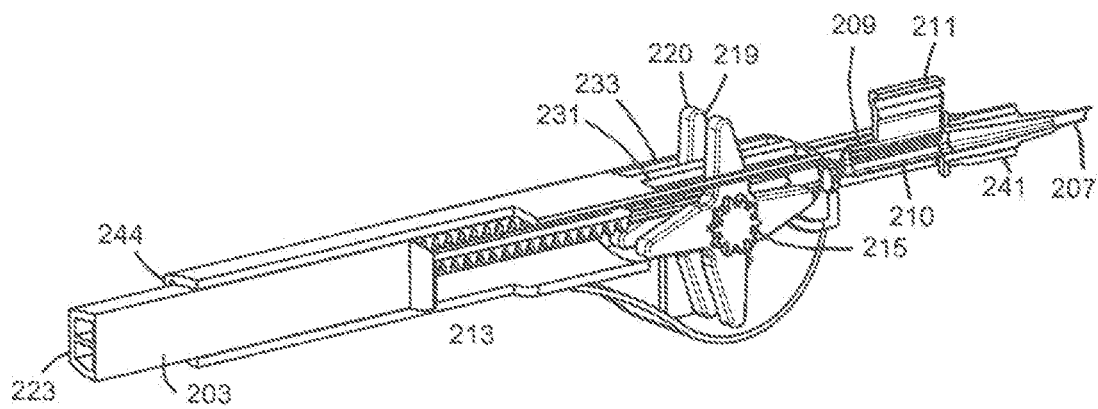
FIG. 13 is a sectional view of the further injector according to the invention from FIG. 11, and piston rod in a first position (normal position)
Figure 14:
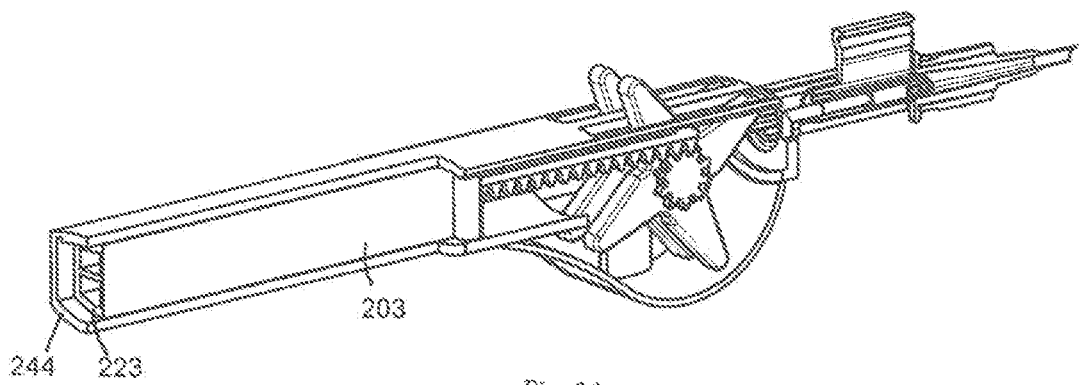
FIG. 14 is a sectional view of the further injector according to the invention from FIG. 11, and piston rod in a second position (start position)
Figure 15:
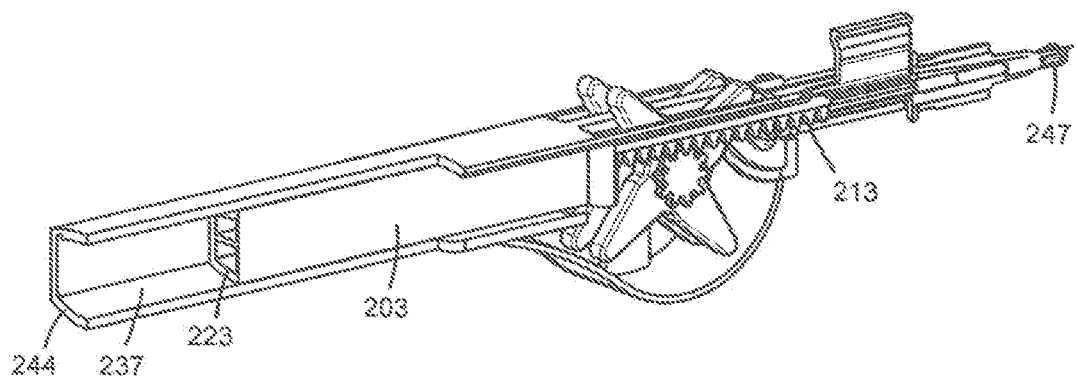
FIG. 15 is a sectional view of the further injector according to the invention from FIG. 11, and piston rod in a third position (end position)

In a third exemplary embodiment FIG. 11 shows diagrammatically in an oblique view an injector 201 with a gear train, in particular a rack gearing, for an intraocular lens. In FIG. 12, the injector 201 is shown in an exploded view. FIGS. 13, 14 and 15 show in each case a sectional view of the injector 201 with a different position of the piston rod 203. Hereinafter in particular differences of this third exemplary embodiment according to FIGS. 11-15 compared to the previously described two exemplary embodiments according to FIGS. 1-5 or FIGS. 6-10 will be discussed.

The injector 201 includes a longitudinal housing 205 with a nozzle 207 at the end of the housing, wherein a displaceable piston rod 203 is supported in the housing 205 and wherein said piston rod 203 can be displaced forwards in the direction of the nozzle 207 in order to eject a lens through the nozzle 207 (FIGS. 12-15).

A gear rack 213 (implemented for example as a pair of gear racks) is formed on the piston 203, which cooperates with a toothed gear 215 (formed for example as a pair of toothed gears). The gear rack 213 and toothed gear 215 form a transmission mechanism, in particular a rack gearing. By manually actuating the toothed gear 215 the piston 203 can be moved backwards and forwards in so far as the teeth of the gear rack 213 and toothed gear 215 inter-engage. The toothed gear 215 is manually driven by means of at least one actuating element 219, which is rigidly connected to the toothed gear 215 or the pair of toothed gears. The actuating element 219 is formed as a lever, advantageously as a lever wheel enlarged compared to the diameter of the toothed gear 15, in particular as a butterfly wheel with radially projecting gripping parts 220.

The toothed gear 215 has a rotation shaft 217. The actuating element 19 advantageously has the same rotation axis 217. The rotation axis 217 of the toothed gear 215 is supported in the housing 205. In order to support the rotation shaft 217 of the toothed gear 215 an indentation 221 is provided in the housing 205. The actuating element 219 and in particular the individual gripping parts 220 of the actuating element project at least partially from the housing 205, whereas the toothed gear 215 is positioned within the circumference of the housing or within the housing 205, i.e. completely in the interior of the housing 205. For the complete accommodation of the transmission mechanism in the housing 205 the housing 205 is formed arched around the toothed gear 215. The housing has however openings 231, 233 for the actuating element 219 and in particular its gripping parts 220, so that the actuating element 219 can be manually operated.

The toothed gear 215 is on account of its function arranged on the teeth row side of the gear rack 213 (i.e. on the gear rack side), optionally at an extension of the gear rack displacement part, over the row of teeth of the gear rack 213 so that the teeth of the toothed gear 215 engage or can engage in the teeth of the gear rack 213. On account of the hosing structure access to the actuating element 219 is however allowed on the rear side of the gear rack. Accordingly, in this third embodiment with only one toothed gear 215 the actuating movement for advancing the piston rod 203 is a pushing movement. The finger pushing movement and the resulting forward driving movement of the piston rod 203 are correlated.

The housing 205 has a proximal opening 244. The piston rod 203 can be inserted through this opening 244 into the housing 205 and in its normal position projects beyond the proximal opening 244 from the housing 205 (FIG. 13).

By manually pushing the piston rod 203 at its proximal end 223 the piston rod 203 can (similar to pushing the sliding element 23 in the first exemplary embodiment, FIG. 3 or pushing the proximal end 123 in the second exemplary embodiment, FIG. 8) be displaced manually from the normal position (FIG. 13) to a start position or somewhat further by continuing to push (FIG. 14). From the start position (FIG. 14) the piston rod 203 can then in a second step be displaced further forwardly in a controlled manner by means of the actuating element 219 in the direction of the nozzle 207.

The housing 205 is advantageously composed of for example at least one first housing part and a second housing part, such as an upper housing part 227 and a lower housing part 229, which can be assembled or interlocked. The rotation shaft 217 of the toothed gear 215 is supported in an indentation 21 in the lower housing part 229. On the other hand, the upper housing part 227 has opening 231 and 233 for the actuating element 219 and in particular the gripping parts 220 of the actuating element 219. The proximal opening 224 is formed in the upper housing part 227, which immediately following the opening 224 has a receptacle 237 for the piston rod 203, into which the piston rod 203 can be inserted. The lower housing part 229 together with inserted toothed gear 215 and actuating element 219 can before or after the insertion of the piston rod 203 into the upper housing part 227 be assembled together with the upper housing part 227. The point of access to the actuating element 219 is provided on the upper housing part and is designated by the operating region 236.

In the present third embodiment a support 239 with nozzle hole 241 and cartridge receptacle 243 is formed on the nozzle side on the upper housing part 227.

The mode of operation of the injector 201 can be seen from FIGS. 13, 14 and 15.

The injector 201 also serves in particular for injecting an intraocular lens into an eye. Similarly to the first exemplary embodiment, in the third exemplary embodiment the drive of the piston rod 203 is effected via at least one toothed gear 215, which engages on a gear rack 213 and moves the piston rod 203 forwards. The injector 201 is in this connection held in one hand (for example like a ballpoint pen) and the toothed gear 215 and in particular its actuating element 219 are moved with a finger of the same hand (e.g. with the index finger). In the implementation, according to FIGS. 11-15, the actuating element 219, which is formed as a butterfly wheel, can be turned with the finger in several pushing movements so that the gear rack 213 and thus the piston rod 203 (in particular opposed to the pulling movement of the finger) is moved towards the nozzle 207 and thereby displaces the lens in the direction of the nozzle 207 and ejects it from the latter (FIG. 15). Also in this third exemplary embodiment (FIGS. 13-15) the ejection of the lens on driving the forward movement of the piston 203 via the gear train proceeds in a controlled manner, while the doctor simply requires one hand to hold the injector and to eject the lens. The second hand is free for other manipulations on the patient. Fine pushing movements of a finger on the butterfly wheel are sufficient to introduce the lens into an eye.

The dimensions of the lens and/or the plunger usually are larger than the distal nozzle end (i.e. the nozzle outlet opening). Therefore, the lens and/or the deformable plunger are compressed and/or deformed during the process of ejection of the lens. For the purpose of pushing the lens through the nozzle the lens is folded, within the loading device already. Between the nozzle 7 and the lens and/or between the nozzle 7 and the tappet 47 friction occurs during the ejection of the lens. The friction forces may result in a rebound effect of the lens and/or the tappet 47 and, consequently, in a rebound effect of the piston rod 3.

In practice during use of an injector 1, 101, 201 the actuating element 19, 119, 219 may be actuated by several strokes of one single finger (i.e. one of the surgeon's finger). Thereby the actuating element 19, 119, 219 is moved in an interrupted manner, as the actuating element 19, 119, 219 is released by the finger in-between two strokes. However, while the actuating element 19, 119, 219 is released, it may occur that the piston rod 3, 103, 203 slides back e.g. due to a resilience in the tappet and/or the lens, in particular due to the above mentioned rebound effect. Thereby the tappet and/or the lens extends, as soon as the forward pressure applied via the actuating element 19, 119, 219 is omitted, and in consequence (i.e. due to the rebound effect) the piston rod 3, 103, 203 is pushed backwards. Together with the piston rod 3, 103, 203 the actuating element 19, 119, 219 rotates. Especially when a butterfly wheel is used this may mean that the surgeon cannot even grab the next wing of the butterfly wheel but e.g. only the wing that was pressed by him just before the rebound. Such rebound effect and therewith a back movement of the piston rod 3, 103, 203 and a respective movement of the actuating element can be reduced or prevented e.g. by employing a ratchet mechanism.

During manual operation of an injector, in particular during manual driving or pushing of the lens by means of a gear transmission, such rebound effect, in particular said resilience of the tappet and/or the lens, may be problematic, especially since high precision is required during eye surgery. However this problem advantageously may be overcome by integrating a ratchet mechanism as described herein.

Injectors comprising a ratchet mechanism were found particularly advantageous for injecting a lens via a small incision, e.g. incisions equal or smaller than 2 mm, e.g. a 1.8 mm incision. Respective advantageous injectors comprise a nozzle with a distal nozzle end having a cross section smaller than 3.1416 mm$^2$ (i.e. smaller than the surface of a circle of a diameter of 2 mm or smaller than an ellipse of 3.1416 mm$^2$). In particular, a ratchet mechanism is preferred in injectors which comprise a piston rod with an elastic tappet (i.e. plunger), such as e.g. a silicon tappet. Without ratchet mechanism, it may happen that the piston rod is pushed rearward—in a spring like manner—by the elastic tappet and/or lens when the tappet and/or lens is compressed, e.g. due to a resistance in the ejecting nozzle or the eye tissue. Such backward motion of the piston rod can be stopped or prevented by a ratchet mechanism. A ratchet mechanism is of particular advantage for injectors with an elastic tappet and a distal nozzle end having a relatively small cross section.

If the piston rod tip is hard, i.e. incompressible, or has a large elastic tappet for a large nozzle end the risk of a rebound is lower. However for safety reasons a ratchet mechanism may still be valuable.

In the following are presented exemplary injectors with a ratchet mechanism.

Figure 16:
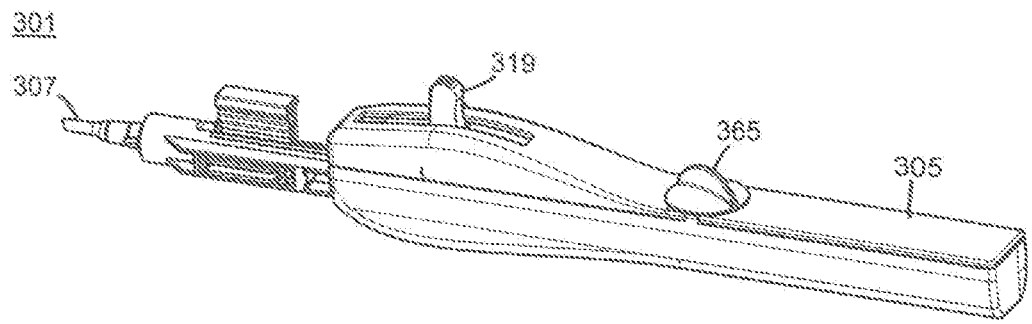
FIG. 16 is an oblique view of an injector according to the invention comprising a ratchet mechanism.
Figure 17:
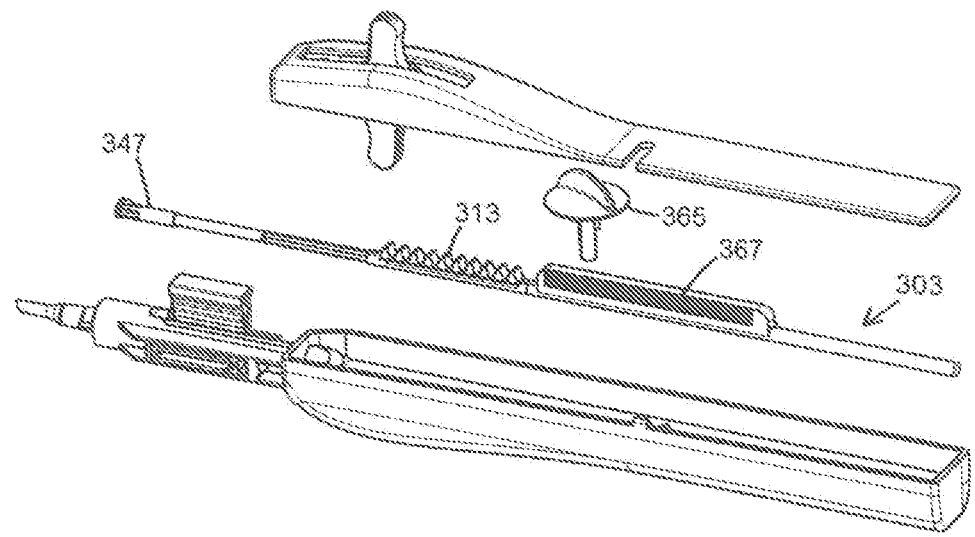
FIG. 17 is an exploded view of an injector according to the invention comprising a ratchet mechanism.
Figure 18:
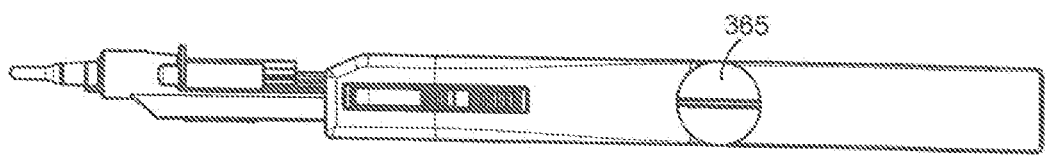
FIG. 18 is a top view of an injector according to the invention comprising a ratchet mechanism, with the ratchet mechanism inactivated.
Figure 19:
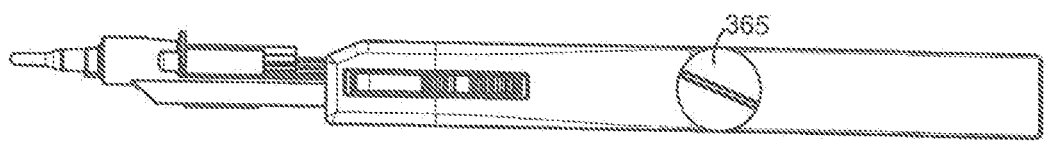
FIG. 19 is an . . . view of an injector according to the invention comprising a ratchet mechanism, with the ratchet mechanism in its active position.

In a fourth exemplary embodiment as presented in FIGS. 16-21, FIG. 16 shows schematically in an oblique view an injector 301 with a gear train, in particular a rack gearing, and a ratchet mechanism for an intraocular lens. In FIG. 17 the injector is illustrated in an exploded view. FIGS. 18, and 19 show in each case a top view of the injector 1 with a different setting of the ratchet mechanism—FIG. 18. with the ratchet mechanism inactivated and FIG. 19 with the ratchet mechanism activated.

Figure 20:
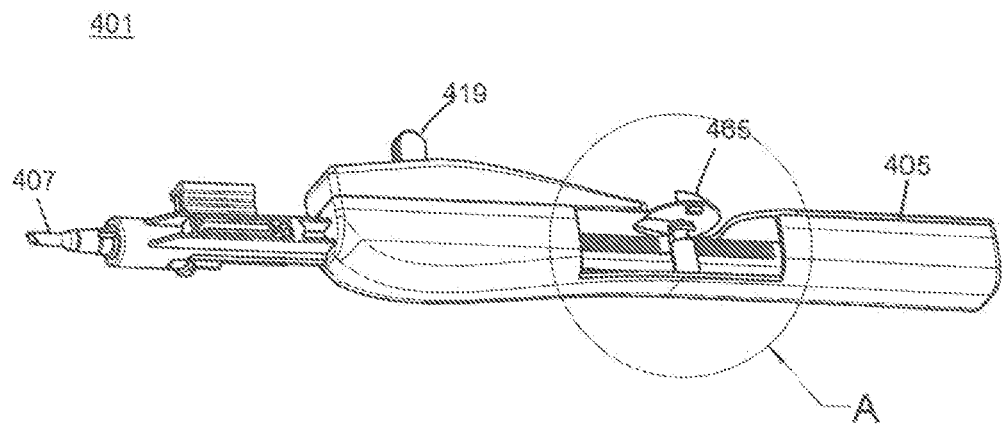
FIG. 20 is a cutaway drawing of a further injector according to the invention comprising a ratchet mechanism, with the ratchet mechanism in its active position.
Figure 21:
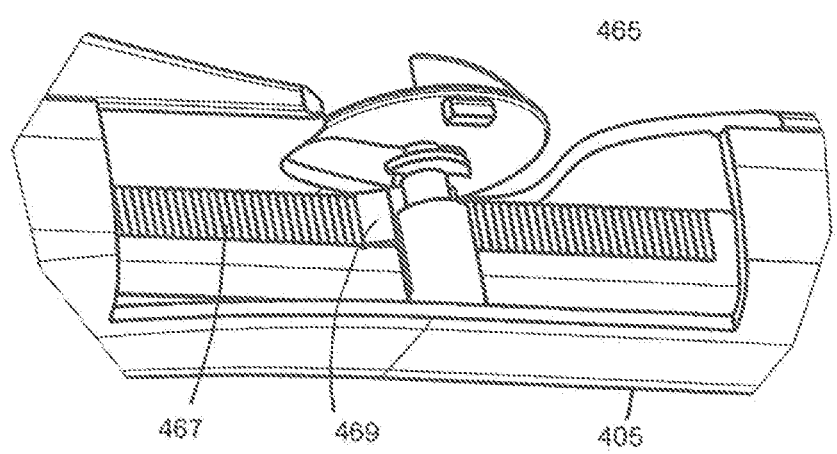
FIG. 21 is an enlarged view of detail A of FIG. 20.

Similar to FIG. 16, FIG. 20 shows schematically in an oblique cutaway view an injector 401 with a gear train, in particular a rack gearing, and a ratchet mechanism for an intraocular lens. For the purpose of presentation, a part of the housing 405 is selectively removed to make internal features, in particular the features of the ratchet mechanism, visible. FIG. 21 shows a detailed view of the ratchet mechanism within the housing 405. The ratchet mechanism as presented in FIGS. 20 and 21 is in its activated setting.

The injector 301, 401 includes a longitudinal housing 305, 405 with a loading chamber 309, 409 for a lens and with a nozzle 307, 407 located at the end of the housing 305, 403, the nozzle 307, 407 forming the front part of the injector 301, 401. A displaceable piston rod 303, 403 is supported in the housing 305, 405, the piston rod 303, 403 can be driven forwardly through the loading chamber 309, 409 and in the direction of the nozzle 307, 407 in order to eject a lens through the nozzle. Hereby the forward moving piston rod 303, 403 pushes the lens from the loading chamber 309, 409 towards the nozzle exit.

The ratchet mechanism allows a continuous linear motion of the piston rod 303, 403 in one direction only, i.e. a forward movement of the piston rod 303, 403 towards the nozzle 307, 407, while preventing motion of the piston rod 303, 403 in the opposite direction. The ratchet mechanism comprises e.g. a linear rack 367, 467 (ratchet rack) with teeth and a pawl (or click) 469, e.g. designed as a pivoting, spring-loaded finger, that engages the teeth of the rack 367, 467. The ratchet rack 367, 467 is a structure formed on the piston rod 303, 403. With regard to the piston rod tip, the ratchet rack 367, 467 is placed further back than the gear rack 313, 413. The pawl 569 is fixedly attached to the housing 305, 405, so that pawl 469 and rack 367, 467 are engaged at the same time when gear rack 313 and actuating element 319 of the transmission mechanism are engaged. When the piston rod 303, 403 and therefore the ratchet rack 367, 467 is moving in the unrestricted direction (i.e. forward in direction towards the nozzle 307, 407), the pawl 469 easily slides over the teeth of the rack 367, 467, spring force forcing the pawl 469 against the rack 367, 467 into the depression in-between the teeth as it passes the tip of each tooth. Alternatively, instead of a rack with teeth a smooth, toothless rack with a high friction surface may be used. Hereby the pawl bears against the surface at an angle so that any backward motion causes the pawl to jam against the surface and thus prevent any further backward motion.

In the event that the lens and/or tappet 347, 447 gets stuck or pressed, for example when lens and tappet are forced into the narrowing channel of the nozzle 307, 407, the tappet's or lens's intrinsic resiliency causes a repulsive force acting on the piston rod 303, 403. If in this situation the manual, forward activating action on the actuator 319, 419 is interrupted, then the ratchet mechanism prevents any substantial backward motion of the piston rod 303, 403, in that the pawl 469 locks against the ratchet's rack 367.

Optionally the pawl is fixed on a ratchet mechanism actuating element 365, 465, which allows to manually inactivate the ratchet mechanism by disengaging pawl 469 and rack 367, 467. The actuating element 365, 465 of the ratchet mechanism is placed further away from the nozzle 307, 407 than the actuating element 319, 419 of the transmission mechanism, thus behind the actuating element 319, 419 of the transmission mechanism.

A ratchet mechanism may be combined with any of the herein presented transmission mechanisms for the purpose stated.

Instead of or in addition to above mentioned ratchet mechanism for preventing any repulsive effects to influence the position of the actuation element or for reducing any such effects on the position of the actuation element, sliding friction forces may be employed. For example axle bearings (for example of rotation shafts 17, 117, 118, 217 and indentations 21, 121, 122, 221, respectively) may be designed with extra friction so that a possible repulsive effect is damped or absorbed due to friction.

Whereas hereinbefore specific embodiments have been described, it is obvious that different combinations of the illustrated realisation possibilities can be employed insofar as they are not mutually contradictory.

Whereas the invention has been described hereinbefore with reference to specific embodiments, it is obvious that changes, modifications, variations and combinations can be made without departing from the concept of the invention.

The invention claimed is:

1. An injector for ejecting an intraocular lens and injecting the intraocular lens into an eye, comprising:
    an injector body within which an injector piston rod can be guided in an axially displaceable manner;
    an injector nozzle located at a front end of the injector body and positioned in a direction within which the injector piston rod can be displaced;
    a displacement mechanism for pushing the injector piston rod in a forward direction toward the injector nozzle; and
    an actuating element located at an operating region formed at a longitudinal side of the injector body for manual actuation of the displacement mechanism, the displacement mechanism including a transmission mechanism comprising a rack and at least one first pinion, the rack being a part of the injector piston rod and the at least one first pinion being fastened to the actuating element, placing the actuating element and the injector piston rod in an articulated driving connection, so that the rack and the at least one first pinion engage with one another to transmit a manual driving force from the actuating element to the piston rod;
    a ratchet mechanism comprising a linear rack structure on the injector piston rod;
    a pawl attached to the injector body, the pawl being positionable between an inactivated pawl position, where the pawl and the linear rack structure are disengaged, and an activated pawl position, where the pawl and the linear rack structure are engaged, such that in the inactivated pawl position, a forward and a backward movement of the piston rod is possible depending on a direction of an operator's movement of the actuating element, and in the activated pawl position a forward movement of the piston rod in the forward direction toward the injector nozzle is possible but a backwards movement of the piston rod in a rearward direction away from the injector nozzle is inhibited by the pawl by engagement with the linear rack structure, whereby, in the activated pawl position, the forward movement of the piston rod in the forward direction toward the injector nozzle results in pushing the intraocular lens out of the injector, while due to inhibition of the backwards movement of the piston rod in a rearward direction away from the injector nozzle retraction of the intraocular lens is prevented.

2. The injector of claim 1, further comprising a ratchet mechanism activating element.

3. The injector of claim 1, further comprising a deformable plunger on a tip of the piston rod.

4. The injector of claim 3, wherein the deformable plunger comprises an elastic or viscoelastic plunger.

5. The injector of claim 1, wherein a distal end of the nozzle comprises has a cross sectional area less than 3.1416 $mm^2$.

6. The injector of claim 1, wherein a distal end of the nozzle comprises has a cross sectional area less than 3.0 $mm^2$.

7. The injector of claim 1, wherein a distal end of the nozzle comprises has a cross sectional area less than 2.8 $mm^2$.

8. The injector of claim 1, wherein the transmission mechanism comprises a gear train.

9. The injector of claim 1, wherein the actuating element can be operated by manually pushing or pulling in a longitudinal direction of the injector body.

10. The injector of claim 1, further comprising a second pinion arranged between the at least one first pinion and the rack whereby teeth of the second pinion engage on the one hand with teeth on the at least one first pinion and on the other hand with teeth of the rack so that a driving force is transmitted by the second pinion from the first at least one pinion to the rack.

11. The injector of claim 10, wherein the second pinion is operated as a spur gear.

12. The injector of claim 1, wherein the first pinion is drivable by the actuating element.

13. The injector of claim 12, wherein the actuating element is fastened as an operating lever to the first pinion.

14. The injector of claim 1, wherein the first pinion is operated as a spur gear.

15. The injector of claim 1, wherein the injector body defines at least one opening in the operating region in the injector body, by which the actuating element is accessible for manual actuation.

16. The injector of claim 15, wherein at least a portion of the actuating element projects through the at least one opening and from the injector body.

17. The injector of claim 1, wherein the injector is operable with a single hand.

18. The injector of claim 1, wherein the transmission mechanism is a manually operating transmission mechanism.

19. The injector of claim 1, wherein the actuating element comprises a rotating actuating element.

20. The injector of claim 1, wherein the actuating element requires more than one finger stroke to push the interocular lens out of the nozzle.

* * * * *